United States Patent
Allison

(10) Patent No.: US 12,285,239 B2
(45) Date of Patent: Apr. 29, 2025

(54) APPARATUS AND METHOD OF NON-INVASIVELY DETERMINING DEEP TISSUE TEMPERATURE USING MICROWAVE RADIOMETRY

(71) Applicant: Brain Temp, Inc., Bryn Mawr, PA (US)

(72) Inventor: Robert C. Allison, Rancho Palos Verdes, CA (US)

(73) Assignee: Brain Temp, Inc., Bryn Mawr, PA (US)

( * ) Notice: Subject to any disclaimer, the term of this patent is extended or adjusted under 35 U.S.C. 154(b) by 0 days.

(21) Appl. No.: 18/744,588

(22) Filed: Jun. 14, 2024

(65) Prior Publication Data

US 2024/0335121 A1 Oct. 10, 2024

Related U.S. Application Data

(63) Continuation-in-part of application No. 17/153,360, filed on Jan. 20, 2021, now abandoned.

(60) Provisional application No. 62/963,578, filed on Jan. 21, 2020.

(51) Int. Cl.
*A61B 5/01* (2006.01)
*A61B 5/00* (2006.01)

(52) U.S. Cl.
CPC .............. *A61B 5/01* (2013.01); *A61B 5/7203* (2013.01); *A61B 5/7225* (2013.01); *A61B 5/7271* (2013.01); *A61B 5/742* (2013.01); *A61B 2562/0271* (2013.01)

(58) Field of Classification Search
None
See application file for complete search history.

(56) References Cited

U.S. PATENT DOCUMENTS

| | | | |
|---|---|---|---|
| 2012/0029359 A1 | 2/2012 | Sterzer et al. | |
| 2015/0185088 A1* | 7/2015 | Rabieirad | A61B 5/02055 374/122 |
| 2017/0340208 A1 | 11/2017 | Popovic et al. | |
| 2021/0219846 A1* | 7/2021 | Allison | G01K 13/20 |

FOREIGN PATENT DOCUMENTS

JP 2016539752 A 12/2016

OTHER PUBLICATIONS

Stec et al. (A 4.4 GHz Microwave Thermometer With Compensation of Reflection Coefficient; 13th International Conference on Microwaves, Radar and Wireless Communications. MIKON—2000. Conference Proceedings (IEEE Cat. No. 00EX428) (Year: 2000).*

(Continued)

*Primary Examiner* — Jay B Shah
(74) *Attorney, Agent, or Firm* — Bochner PLLC; Andrew D Bochner; Eric R Kleinertz

(57) ABSTRACT

An apparatus for measuring a target tissue temperature is provided. The sensor antenna may include an outside and a contact side. A sensor antenna measurement aperture may be disposed on the contact side. The sensor antenna measurement aperture may be configured to generate a first signal. A skin temperature sensor may be disposed on the contact side and configured to generate a second signal. A radiometer may be configured to receive the first signal and the second signal.

7 Claims, 10 Drawing Sheets

(56) References Cited

OTHER PUBLICATIONS

Stauffer et al. (Stable Microwave Radiometry System for Long Term Monitoring of Deep Tissue Temperature; 2013) (Year: 2013).*
Momenroodaki et al. (Non-Invasive Internal Body Temperature Tracking with Near-Field Microwave Radiometry; 2017) (Year: 2017).*
Office Action of the Japan Patent Office in related Japanese Appl. No. 2022-544374, dated Nov. 12, 2024, 10 pages.

* cited by examiner

APPARATUS AND METHOD OF NON-INVASIVELY DETERMINING DEEP TISSUE TEMPERATURE USING MICROWAVE RADIOMETRY

CROSS-REFERENCE TO RELATED APPLICATIONS

This application is a continuation-in-part of U.S. application Ser. No. 17/153,360, filed Jan. 20, 2021, which is hereby incorporated by reference.

INTRODUCTION

Determining tissue temperature is desirable for diagnosis and treatment of numerous conditions. Conventional diagnostic methods and treatments utilize invasive methods of tissue measurement, which significantly increases risks and recovery, as well as costs. Thus, non-invasive methods of measuring temperature are desired. However, even if with non-invasive methods, it is difficult to ascertain the temperature at a specified location or depth.

In particular, cerebral temperature is a significant indicator in disruptions of important life functions. However, the cerebral temperature is largely inaccessible and therefore not easily measured. Additionally, a human's epidural temperature is lower than the temperature at the center of the brain. Moreover, the temperature of the surface of the brain differs from the temperature at the center of the brain. Thus, even an intrusive measurement at the surface of the brain may not be telling of the temperature at its core.

It would be desirable, therefore, to provide apparatuses, systems, and methods for determining tissue temperature at a specified depth or location, in a non-invasive manner.

SUMMARY

Disclosed herein are systems, apparatuses, and methods for determining temperature of tissue non-invasively.

In an embodiment, the invention of the present disclosure may be an apparatus for measuring a target tissue temperature comprising a sensor antenna having an outside and a contact side. In a further embodiment, the apparatus comprises a sensor antenna measurement aperture disposed on the contact side, where the sensor antenna measurement aperture is configured to generate a first signal. The invention of the present disclosure may further comprise a skin temperature sensor disposed on the contact side, where the skin temperature sensor is configured to generate a second signal. In an embodiment, the apparatus includes a radiometer configured to receive the first signal and the second signal, in electrical communication with the sensor antenna, the sensor antenna measurement aperture, and the skin temperature sensor. The target tissue temperature may be calculated via the equation $T_{target}=T_{skin}+(T_{average}-T_{skin})*c$, where $T_{target}$ is the target tissue temperature, $T_{skin}$ is the patient's skin temperature, $T_{average}$ is the average temperature, and c is a constant.

In further embodiments, the apparatus may include a remote switch module disposed between the sensor antenna and the radiometer. Moreover, in an embodiment, the constant may be determined experimentally based on a preexisting dataset. In even a further embodiment, the average temperature is a weighted average temperature. In such an embodiment, the weighted average temperature may be proportional to the summation of $T_d*A*e^{(-d/c1)}$ from the patient's skin to the target tissue, where d is the variable depth of a tissue, $T_d$ is the temperature at a depth d, A is a constant, and c1 is a constant. Thus, fractional contribution to the weighted average temperature (radiometer temperature) may be calculated from any particular depth.

In one embodiment, the apparatus may further include an isolator, a low noise amplifier, a band pass filter, a microwave detector, a video amp, a synchronous detector, and/or a low pass filter.

In an embodiment, the invention of the present disclosure is a method to measure a target tissue temperature comprising placing a sensor antenna on a patient's skin, where the sensor antenna has a sensor antenna measurement aperture and a skin temperature sensor. In an embodiment, the method may also include detecting, via the sensor antenna, a plurality of microwave emissions from a measurement volume of tissues, where the measurement volume of tissues comprises a plurality of tissue layers. The method may further include detecting, via the skin temperature sensor, a patient's skin temperature. Moreover, the method may include calculating an average temperature of the measurement volume of tissues; and calculating the target tissue temperature via the equation $T_{target}=T_{skin}+(T_{average}-T_{skin})*c$, where $T_{target}$ is the target tissue temperature, $T_{skin}$ is the patient's skin temperature, $T_{average}$ is the average temperature, and c is a constant.

In one embodiment, the constant may be determined experimentally based on a preexisting dataset. In another embodiment, the average temperature may be a weighted average temperature, calculated by weighing the average temperature based on an attenuation level of each of the plurality of tissue layers. In one embodiment, adhesive may be disposed on the sensor antenna.

Figure 1:
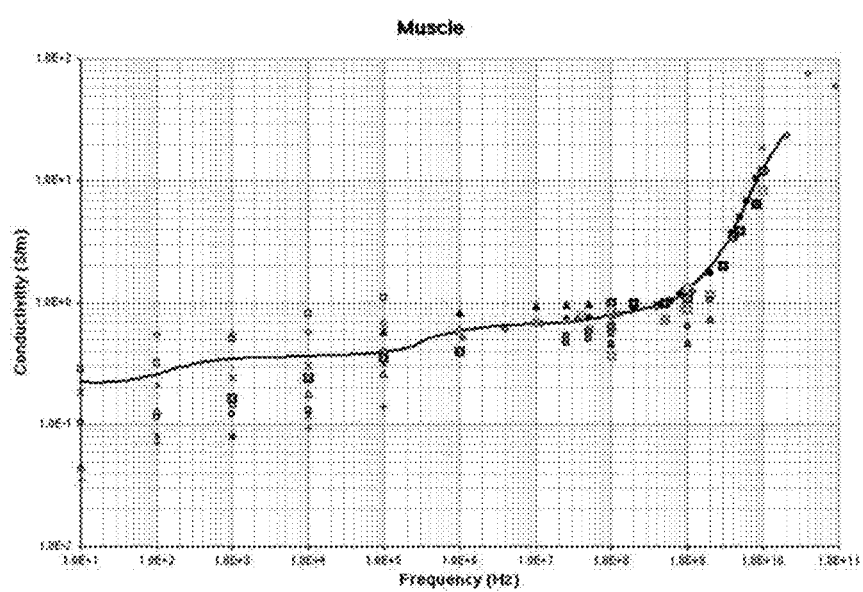
FIG. 1 illustrates a plot of muscle conductivity versus frequency.

While the invention is described with reference to the above drawings, the drawings are intended to be illustrative, and the invention contemplates other embodiments within the spirit of the invention.

DETAILED DESCRIPTION

The present invention will now be described more fully hereinafter with reference to the accompanying drawings which show, by way of illustration, specific embodiments by which the invention may be practiced. This invention may, however, be embodied in many different forms and should not be construed as limited to the embodiments set forth herein; rather, these embodiments are provided so that this disclosure will be thorough and complete, and will fully convey the scope of the invention to those skilled in the art. Among other things, the present invention may be embodied as devices or methods. Accordingly, the present invention may take the form of an entirely hardware embodiment, an entirely software embodiment, or an embodiment combining software and hardware aspects. The following detailed description is, therefore, not to be taken in a limiting sense.

Throughout the specification and claims, the following terms take the meanings explicitly associated herein, unless the context clearly dictates otherwise. The phrases "in one embodiment," "in an embodiment," and the like, as used herein, does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

It is noted that description herein is not intended as an extensive overview, and as such, concepts may be simplified in the interests of clarity and brevity.

All documents mentioned in this application are hereby incorporated by reference in their entirety. Any process described in this application may be performed in any order and may omit any of the steps in the process. Processes may also be combined with other processes or steps of other processes.

Disclosed herein are devices, systems and methods (the "System") for measurement of tissue temperature at varying depths. Devices and methods for determining temperature of tissue non-invasively are hereby provided.

In an embodiment, microwave emission resulting from thermal activity in body tissue may be used to discern the temperature of the tissue non-invasively. The depth beneath the skin from which the microwave emissions may be detected is primarily determined by tissue attenuation resulting from electrical conductivity in the tissue. This attenuation may be frequency dependent.

FIG. 1 illustrates a plot of muscle conductivity versus frequency. Referring to FIG. 1, the conductivity of the muscle is relatively constant up to roughly 1 GHZ. As the frequency surpasses 1 GHz, the conductivity, and therefore the attenuation, begins to increase rapidly.

In an embodiment, a measurement from the skin surface may include the emissions from the total volume of tissue in the sensor reception area, out to a depth where attenuation decreases the magnitude of the emitted energy to an undetectable level. As a non-limiting example, the sensor reception area may be a 1"×1" square disposed on the surface of a patient's skin. In such a non-limiting example, a non-filtered measurement of the emissions would include the sum of emissions from the most outer layer of tissue to the deepest layer that provides readable emission levels. Further, in such a non-limiting example, if the deepest readable layer were 2" deep, the overall total volume of tissue in the reception area would be 2 cubic inches. However, in various embodiments the sensor reception area may be any area and the volume of tissue may be any volume.

In one embodiment, the frequencies where attenuation is lowest will include the deepest temperature contributions. By selecting appropriate detection frequencies, emissions can be measured that include contributions from differing depths. For example, depths of 12-14 millimeters, or any other suitable depth, may be measured.

In an embodiment, temperatures from two or more measurement volumes may be used to determine the temperature in the region where the volume is not common to both (all) measurements. Thus, temperature at a deep region beneath the skin surface may be determined using two temperature measurements. In an embodiment, one microwave measurement may be used, that includes temperature contributions from the region of interest and a skin temperature measurement. In further embodiments, any number of microwave measurements and/or any number of skin temperature measurements may be compounded, weighted, or otherwise used to determine temperature for a desired depth.

In an exemplary embodiment, brain tissue may be targeted. The user of the System may desire a temperature reading at a particular depth of the brain. Thus, temperature measurements at different depths (such as 1 millimeter, 2 millimeter, 4 millimeter, and any other suitable measurements) may be determined. According to an embodiment, a temperature gradient is determined between the deep brain temperature, and temperature at skin surface. However, in alternate embodiments, a temperature gradient may be determined between the deep brain temperature, and any other temperature measured at any region on the body.

Figure 2:
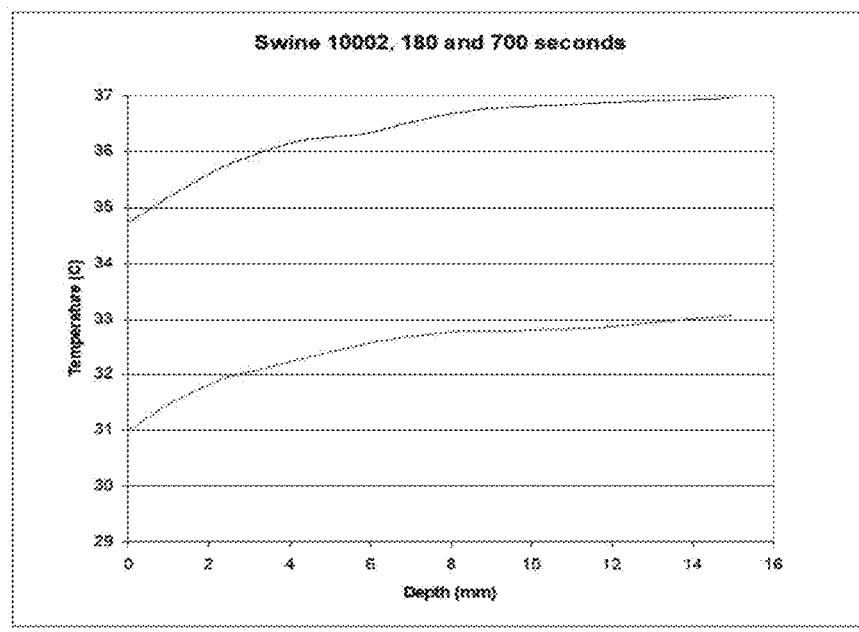
FIG. 2 illustrates a plot of temperature versus depth in live swine beginning from the surface and going to a depth within brain tissue.

In one embodiment, the temperature gradient may be determined using one or more thermocouples, or an array of thermocouples, embedded within skulls of living pigs. However, in various embodiments, the temperature gradient may be collected from various sources. The temperature gradient between the inner temperature and surface temperate may be the result of blood profusion and normal heat flow to the surrounding environment. FIG. 2 illustrates a plot of temperature versus depth beginning from the surface and going to a depth within brain tissue. At a deeper depth, such as around 13 mm, the temperature asymptotically approaches a constant value. However, in alternate embodiments, the ratio between temperature and depth may vary at various depths.

Figure 3:
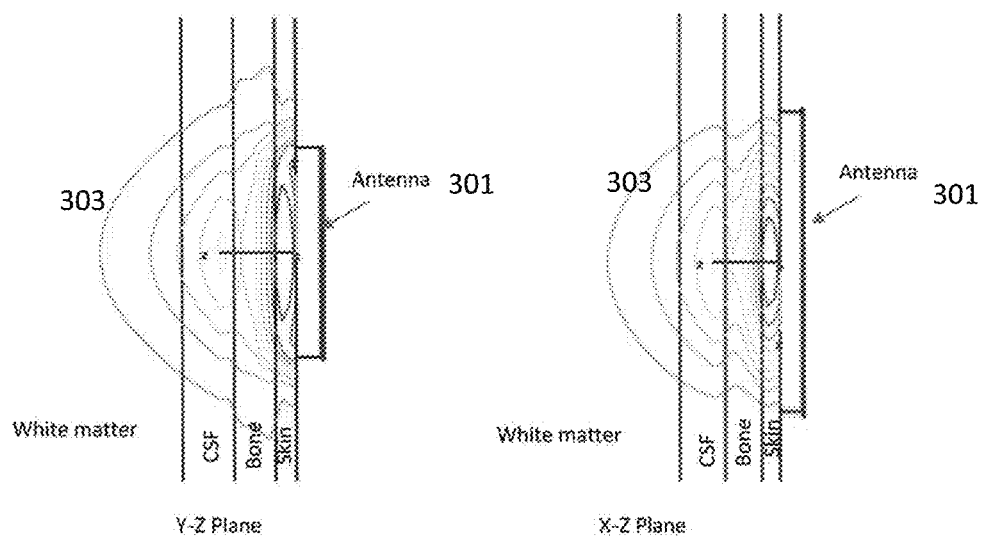
FIG. 3 illustrates a power loss density plot.

In an embodiment, a sensing antenna 301 is used to contact the skin. The sensing antenna 301 that is positioned in contact with the skin may have a reception pattern 303 described by the power loss density plot, as illustrated in FIG. 3.

In an embodiment, power loss density may be determined. The Principle of Reciprocity in Antenna Theory may be used to determine the power loss density. As a non-limiting example, the power loss density is determined as the reciprocal of the sensing pattern. In an embodiment, the power loss density of the microwave signal entering the tissue may describe the contribution from each point in the layers of tissue to the total power received by the antenna. In a further embodiment, the distribution of power loss density may be determined using 3D electromagnetic simulation software. In such an embodiment, the power distribution may be a curve fit to an equation describing the contribution as a function of depth into the layers of tissue. As a non-limiting example, this equation may be: fractional contribution of total received power as a function of depth=$A*e^{(-depth/C)}$, where A and C are constants.

In an embodiment, energy received by the sensor may be determined as a weighted average of the emissions from temperatures within the measurement volume. That is, total received signals from emissions may be shaped by the attenuation in the volume. Emissions from distant tissue may be attenuated so temperature may be weighted towards the closer tissue. However, in an embodiment, the user may tailor the weighted average of the emissions so the temperature may be weighted towards any layer of tissue. In another embodiment, the device may be configured to account for the weighted average without need for the user to intervene or adjust settings.

In an embodiment, the radiometer input received from the antenna is proportional to a summation over all depths of the fraction of signal power received from each layer of depth multiplied by the temperature at that depth. As a non-limiting example, the radiometer temperature may be represented by the equation:

Radiometer Temperature =

$$\sum_{d=0}^{d>4\text{ cm}} \{\text{Temperature at depth } d \times \text{Fractional contribution at depth } d\}$$

In an embodiment, the fractional contribution of total received power as a function of depth may be represented by the equation: $A*e^{(-depth/C)}$, where A and C are constants. However, any variation of equations may be used to represent the radiometer temperature and/or the fractional contribution.

In further embodiments, the apparatus may include a remote switch module disposed between the sensor antenna and the radiometer. Moreover, in an embodiment, the constant may be determined experimentally based on a preexisting dataset. In even a further embodiment, the average temperature is a weighted average temperature. In such an embodiment, the weighted average temperature may be proportional to the summation of $T_d*A*e^{(d/c1)}$ from the patient's skin to the target tissue, where d is the variable depth of a tissue, $T_d$ is the temperature at a depth d, A is a constant, and c1 is a constant. Thus, fractional contribution to the weighted average temperature (radiometer temperature) may be calculated from any particular depth, and multiplied by the temperature at the particular depth. The depths may then be summed.

In an embodiment, brain temperature at a deep depth may be determined by determining an average temperature in a volume that includes both deep brain temperature and a temperature at one end of the temperature gradient curve. In a further embodiment, the average temperature and the temperature at one end (such as the skin), may be used to determine the temperature at the other end (deep depth temperature). At certain depths, temperature may be nearly constant. In one embodiment, a straight line may be substituted between the end point temperatures for the weighted average temperature curve. In an alternate embodiment, a line of best fit (including a curved line) may be substituted between any temperatures for the weighted average temperature curve. An exemplary calculation for determining deep brain temperature may be as follows:

$$T_{brain} = T_{skin} + (T_{average} - T_{skin}) \times 2$$

In an embodiment where a weighted average temperature is used, the constant value of "2" may be changed, depending on microwave tissue properties and geometry. In another embodiment, using 3D EM simulation software, the constant may be determined by calculating the power loss density in the measurement volume, multiplying each point in the volume by the temperature at that point, and integrating over the entire volume to find the weighted average temperature. Alternatively, a constant may be calculated by experimentally determining the constant using live animal measurements. However, in alternate embodiments, the constant may be calculated using any combination of theoretical, calculated, hypothesized, or experimental data sets.

In another embodiment, the aforementioned constant may be the Head Factor (HF). In such an embodiment, the HF may be a function of the thermal properties of the skull or other layer and the microwave tissue properties within the skull or other tissue. In an embodiment, the initial value was determined from an animal trial measurement and from electromagnetic simulations using published values on microwave tissue properties.

Therefore, in accordance with the invention, a microwave antenna may be used for determining deep tissue temperature in the brain, at a specified depth, and implement the methods above. The microwave antenna may include a thermistor for measuring skin surface temperature. The microwave antenna or System may further be in communication with an external monitor or computer. In alternative embodiments, there may be more than one microwave antennas or more than one sensors. In further embodiments, the device may include any number or combination of processors, memory units, electronic storage devices, or other electronic components.

In an embodiment, selecting an operating frequency band where potentially interfering devices are not allowed to operate may mitigate unwanted microwave noise. Further, the antenna aperture may be shielded from external sources. In such an embodiment, the shielding may involve configuring the antenna such that outside interference has to propagate through enough tissue layers before reaching the aperture, allowing the unwanted signal to diminish to undetectable levels.

In an embodiment, the magnitude of the microwave emissions collected from a portion of tissue by the sensor antenna is converted to a temperature indication by a microwave radiometer. In an embodiment, the radiometer measurement frequency is selected for measurement depth and other practical considerations such as antenna size and avoidance of potentially interfering electronic devices.

Figure 4:
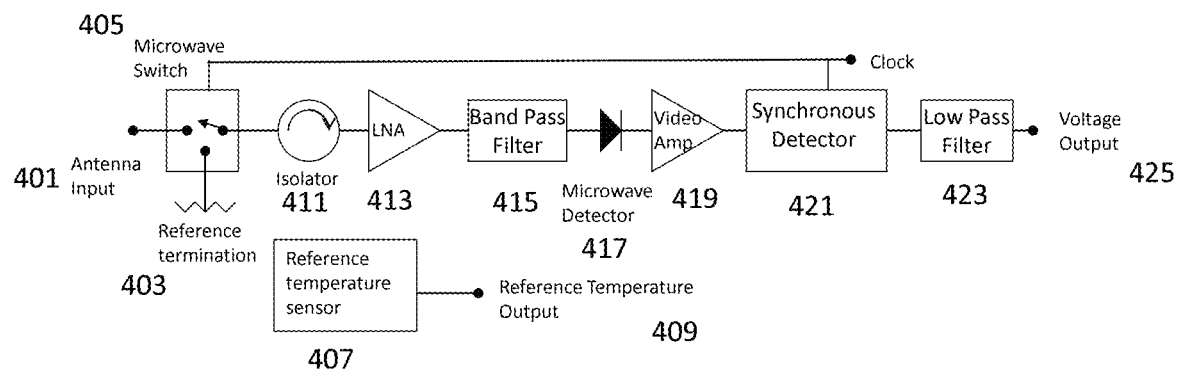
FIG. 4 illustrates a block diagram of an embodiment of the present invention having a radiometer.

FIG. 4 illustrates an embodiment of a radiometer block diagram 400. In an embodiment, a microwave switch 405 alternately selects between the antenna input 401 and a reference termination 403 of known temperature at a 50% duty factor clock rate, which may enable the use of synchronous detection during signal processing. In a further embodiment, a temperature sensor 407 is located adjacent to a reference termination 403 and measures the reference temperature. In an embodiment, the signal next is passed through an isolator 411. In an embodiment, the switch output is amplified by a low noise amplifier 413 and is filtered (for example, through a band pass filter 415). Further, a microwave detector 417 may detect the modulation created by the switch 405.

In an embodiment, a video amp 419 may be positioned after the microwave detector 417. The video amp 419 may be a low frequency AC amplifier. The video amp 419 may be configured to amplify the detector output voltage, which may be 100 Hz but may be higher (for example, 1 Khz or 10 Khz). The video amp 419 may allow for no DC component of a signal to pass. The frequency threshold of the video amp 419 may be set in relation to the switch modulation rate. The modulation may then be filtered and rectified by a synchronous detector 421. In an embodiment, the output is low pass filtered via a low pass filter 423, resulting in a DC voltage 425 proportional to the temperature difference between the antenna input 401 from the head and the reference termination 403. The temperature difference may be added to the reference temperature sensor output 409, resulting in the radiometer temperature.

Figure 5:
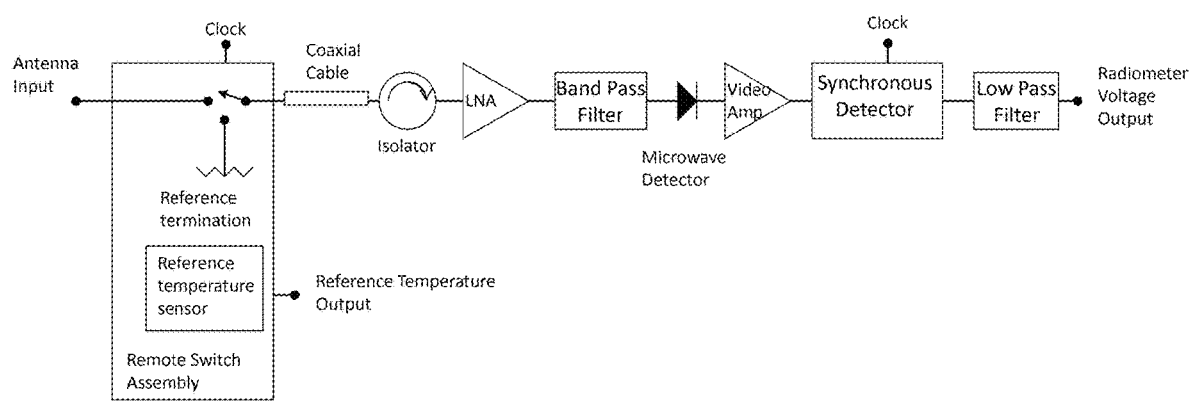
FIG. 5 illustrates a block diagram of an embodiment of the present invention having a radiometer and a remote switch.

FIG. 5 illustrates an embodiment of a radiometer block diagram 500 including a remote switch assembly 501. In such an embodiment, the remote antenna may provide for convenience and comfort to the patient. As a non-limiting example, in the remotely located antenna and switch embodiment, the bulk of the weight of the radiometer is not hanging on the patient's skin. The remotely located switch may also minimize the temperature errors introduced by the coaxial cable that separates the antenna and switch from the radiometer housing.

Figure 6:
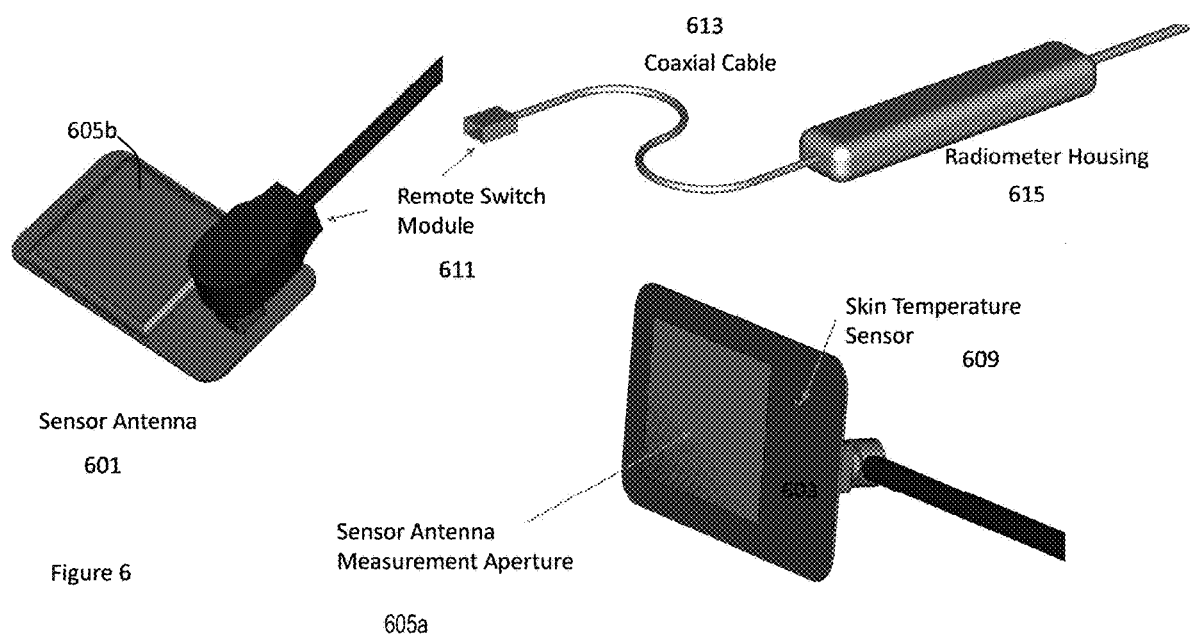
FIG. 6 illustrates an embodiment of the sensor antenna with switch component attached.

FIG. 6 illustrates an embodiment of the sensor antenna 601 including the switch component. In such an embodiment, the antenna 601 is a separable, disposable item. In a further embodiment, the face of the adhesively attached antenna 601 may include the receiving aperture 605a and a skin temperature sensor 609. The skin temperature sensor 609 may be a thermistor, thermocouple, or other small temperature measurement device. In alternative embodiments, any number or type of components may be disposed on the remote switch module 611.

The sensor antenna 601 may have a contact side 603 and an outside 605b. The contact side 603 may be configured to index with a patient's skin. The outside 605b may face away from the patient. The contact side 603 of the sensor antenna 601 may be coated with an adhesive, such that the sensor antenna 601 adheres to the patient's skin. However, in alternate embodiments, the sensor antenna 601 may be held in place with any number of methods. In an embodiment, the contact side 603 of the sensor antenna 601 may include a sensor antenna measurement aperture 605a and/or a skin temperature sensor 609.

In an embodiment, the sensor antenna is connected to the remote switch module 611. In an embodiment the remote switch module 611 is further connected to the radiometer housing 615 utilizing a coaxial cable 613. However, in alternate embodiments, any number of electronic communications tethers may be used. In yet further embodiments, any suitable form of low-loss microwave transmission lines may be used.

In one embodiment, the coaxial cable 613 may comprise a length suitable to transfer signals between the remote switch module 611 and the radiometer housing 615. As a person of ordinary skill will recognize, cables, such as coaxial cables, contribute to signal degradation between the connected devices. As a result, typical coaxial cables are generally limited in length, which in clinical settings, crowds the working field and limits use of the device. Thus, there is a need to provide a wired means of signal transfer, while providing an increased working field and reducing signal degradation.

Some coaxial cables have shown improved signal preservation properties across increased lengths. Further, the radiometer may be configured to compensate for degradation of signal caused by increased coaxial cable lengths (e.g., as described below in relation to FIG. 7). As a result, the remote switch module 611 can be positioned further away from the radiometer housing 615, for example, providing adequate cable slack in instances where a patient may unintentionally tug at said cable. As a nonlimiting example, the system described herein may be adapted for use with infants, such as neonates, and children. In one embodiment, the coaxial cable 613 may be greater or equal to about 2 feet in length. Of course, in other embodiments, the coaxial cable 613 may be less than about 2 feet in length.

Figure 7:
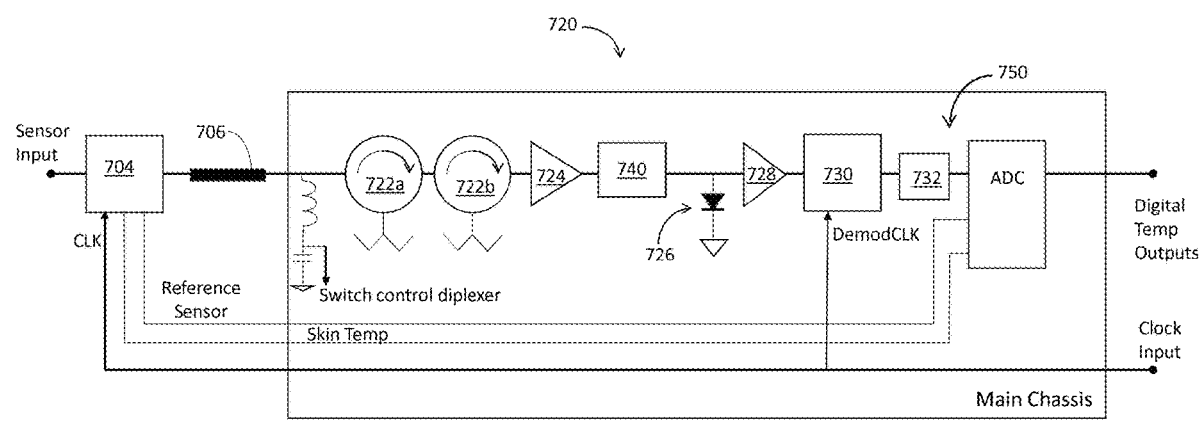
FIG. 7 illustrates a block diagram of an embodiment of a radiometer.

FIG. 7 illustrates a block diagram of one embodiment of a device 700. The device comprises a sensor input 702 coupled to a remote switch module 704, and a coaxial cable 706 coupling the remote switch module 704 to a radiometer 720. In the embodiments illustrated, the remote switch module 704 is further coupled to a clock, a reference sensor, and a skin temperature sensor.

The radiometer 720 may comprise at least one circulator 722a, 722b, a low noise amplifier (LNA) 724, a frequency filter 740, a radio frequency (RF) detector 726, a video amplifier 728, a synchronous detector 730, and a low pass filter 732. Any of the components of the radiometer 720 may comprise any of the characteristics described with reference to FIG. 4.

The LNA 724 is configured, in some embodiments, to receive a signal transmitted by the sensor antenna. The signal corresponds to an electromagnetic noise emitting from the target tissue, for example, the brain tissue. It is contemplated that the electromagnetic noise is related to the absolute temperature (e.g., the sum of tissue temperature, ambient temperature, and noise) and is processed by the LNA 724 and other components of the radiometer 720 to determine a temperature of the target tissue. The LNA 724 may amplify the signal transmitted by the sensor antenna to a level that can be detected and, thus, processed. The LNA 724 may, in some embodiments, amplify the input received from the coaxial cable 706 to permit detection of the signal. In one embodiment, the LNA 724 may provide an amplified gain that establishes a noise floor. It is contemplated that in order to provide a less noisy amplifier, and thus a less noisy system, the noise floor should be low to permit the largest signal gain between the amplifier and the detector. As a result, in some embodiments, the LNA 724 may have a low noise floor. It is contemplated that, in some embodiments, the LNA 724 may compensate for any signal degraded by the coaxial cable 706. The signal may be degraded, for example through the introduction of noise, at the coaxial cable 706, or a loss of the signal. Thus, the noise floor may be set to capture the degraded signal to permit processing and detection of the target tissue temperature as discussed herein.

In one embodiment, the LNA 724 may select frequencies of up to about 4 gHz. Of course, other frequencies are contemplated and may be utilized.

Figure 8:
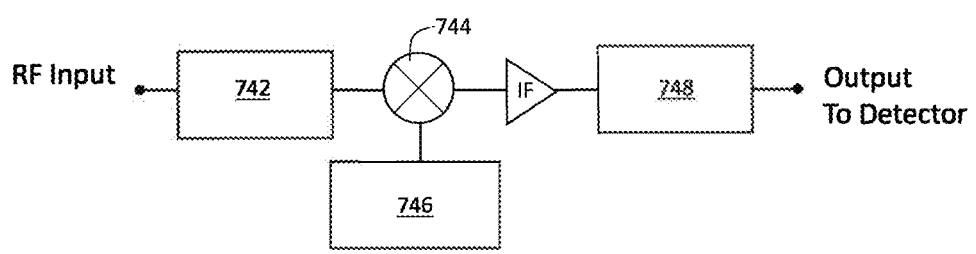
FIG. 8 illustrates a block diagram of one embodiment of a frequency filter.

FIG. 8 shows a block diagram of one embodiment of the frequency filter 740 as illustrated in FIG. 7. The frequency filter 740 comprises an RF band pass filter 742, a frequency mixer 744, a fixed frequency oscillator 746, and an intermediate frequency band pass filter 748. The frequency filter 740 receives an RF input from the remote switch module 704. As illustrated by FIG. 7, the RF input may be the switch output transformed by the at least one circulator 722a,b. The switch output may be amplified by the LNA 724. However, in another embodiment, not illustrated, the frequency filter may receive the switch output without prior processing.

Returning to FIG. 8, the frequency filter 740 may be configured to convert the signal received by the switch output into an intermediate frequency. It is contemplated that the intermediate frequency may narrow the frequency from the switch output to less than the total frequency. More particularly, the frequency filter 740 may remove noise or other contaminants present in the signal received from the switch output. By removing the excess noise and other contaminants from the signal, it is contemplated that the frequency may be reduced to frequencies relevant for determining the tissue temperature. For example, the frequency filter 740 may be configured to remove frequencies from surrounding equipment, such as common medical equipment, to reduce noise contamination in the system.

The frequency filter 740 may reduce the signal to less than all the frequency received from the switch output. For example, the frequency filter 740 may filter approximately up to 1%, 10%, 20%, 30%, 40%, 50%, 60%, 70%, 80%, 90%, or even 99% of the signal. Filtering the signal may provide a narrow range of frequencies that can be detected by the system. It is contemplated that filtering may reduce the detected frequencies to those that comprise the signal generated by the target tissue. In an embodiment, the frequency filter 740 may utilize a cutoff frequency. In a further embodiment, the frequency filter 740 may utilize a percentage bandwidth filter wherein the signal is a percentage of a center frequency. For example, the frequency filter 740 may receive a 1700 megahertz intermediate frequency signal and may utilize an approximately a 10% filter to reduce the signal. Of course, other intermediate frequencies and filters are contemplated and the aforementioned are provided as a nonlimiting example only.

The frequency mixer 744 may be coupled to the frequency oscillator 746. In some embodiments, the frequency mixer 744 and the fixed frequency oscillator 746 may convert the RF input into the intermediate frequency. In one embodiment, the oscillator frequency may be a fixed frequency that has a known oscillation frequency, and the intermediate frequency may be a difference between the RF input and the oscillation frequency. However, in other embodiments, the oscillation frequency may be adjustable, such that the frequency may be any number of known frequencies. It is contemplated that any frequency that is known, whether inherently or through measurement, may be utilized by the frequency oscillator 746. For example, the oscillation frequency may be about 2.33 gHz.

The intermediate frequency may be passed through an intermediate frequency band pass filter 748. In one embodiment, the intermediate band pass filter 748 may reduce the frequency in the system. For example, the intermediate band pass filter 748 may reduce the frequency to less than the frequency received by the intermediate band pass filter 748. For example, the intermediate band pass filter 748 may result in about a 10% bandwidth frequency. Of course, other bandwidth frequencies may be utilized, including, for example and without limitation, a 2.5% bandwidth or a 25% bandwidth. Narrowing the frequency with the intermediate frequency band pass filter 748 is contemplated to reduce the presence of frequencies that do not correspond with the signal generated by the target tissue temperature, reducing noise. This may, for example, reduce the presence of frequencies from other medical devices that may be used in a medical setting, interference with mobile devices, or other frequencies that may be detected from the ambient environment.

Following passing through the intermediate frequency band pass filter 748, the intermediate frequency may be passed through any of the RF detector 726, the video amplifier 728, the synchronous detector 730, and the low pass filter 732, according to the manner described herein.

Figure 9:
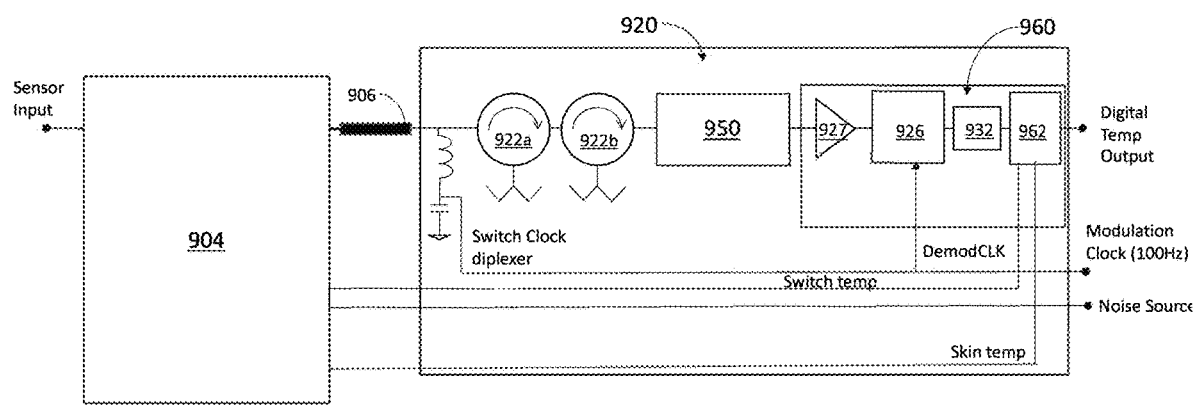
FIG. 9 illustrates a block diagram of one embodiment of a radiometer.

Another embodiment of a radiometer 920 is illustrated in FIG. 9. The radiometer 920 comprises at least one circulator 922a,b, a radiofrequency (RF) board 950, and a signal processor board 960. The signal processor board 960 comprises a video amplifier 927, a synchronous detector 926, a low pass filter 932, and an analog to digital (ADC) convertor 962. The radiometer 920 is illustrated as coupled to a switch 904 via a coaxial cable 906, for example in the manner discussed with reference to FIG. 7.

The synchronous detectors 730, 926, illustrated in FIGS. 8 and 9, may, in some embodiments, convert the AC signal received from the sensor to a DC signal that is proportional to the target tissue temperature.

The low pass filters 732, 932 may, in some embodiments, be configured to filter out transient signals. Transient signals often occur at outer frequencies, but may occur at various points in the signal, and may create noise in the system. In one embodiment, the low pass filter 732, 932 may be configured to filter out an outer frequency of the signal. For example, in one embodiment, the low pass filter 732, 932 may filter out an outer frequency of about 100 Hz. Of course, the low pass filter 732, 932 may filter out any level of the outer frequency. In some embodiments, the low pass filter 732, 932 may be determined by via software, however, in other embodiments, the low pass 732, 932 may be pre-set or otherwise determined.

Figure 10:
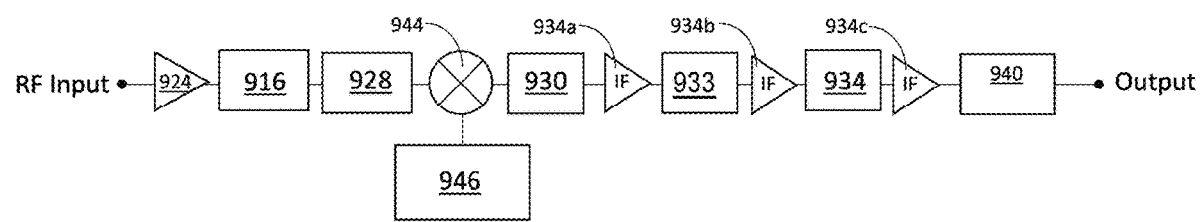
FIG. 10 illustrates a block diagram of an embodiment of an RF board.

FIG. 10 illustrates one embodiment of the RF board 950 illustrated in FIG. 9. The RF board 950 comprises a low noise amplifier (LNA) 924, an RF high pass filter (HPF) 926, an RF low pass filter (LPF) 928, an oscillator 946, a frequency mixer 944, an intermediate frequency (IF) LPF 930, an IF HPF 933, at least one IF band pass filter (BPF) 934a,b,c and at least one intermediate frequency amplifier 936 and an IF detector 940. The components discussed in FIGS. 9 and 10 may comprise any of the characteristics discussed with reference to other figures or otherwise. For example, the LNA 924 may comprise any of the characteristics of the LNA 724 discussed with reference to FIGS. 7 and 8.

Any of the at least one IF band pass filters 934a,b,c may filter the signal to less than all its initial bandwidth. More particularly, the signal may be filtered to a desired bandwidth. Any desired bandwidth is contemplated, for example between about 2.5% to about 25%. In one embodiment, any of the least one IF band pass filters 934a,b,c may reduce the bandwidth to about 10% of the initial bandwidth. For example, the at least one IF band pass filters may, in combination, reduce the initial bandwidth to the desired bandwidth. It is contemplated the reducing the bandwidth may reduce the signal being processed to improve data processing and provide an accurate tissue temperature reading.

In one embodiment, the RF board 950 may receive an RF input from about 2000 to about 90000 Mhz. For example, the RF board 950 may receive an RF input of about 4100±30 Mhz. The RF board 950 may transform the RF input, through oscillation, amplification, and filters to reduce the output. In one embodiment, the RF board 950 may transform the RF input of about 4100±30 Mhz to an output of about 100 Hz. Of course, other input and output values are contemplated and the aforementioned are provided as examples only.

In some embodiments, the RF board 950 may be a frequency filter, such as the frequency filter 740 discussed in FIGS. 7 and 8 and may comprise any of the characteristics discussed or otherwise contemplated.

The signal processing board 960 may comprise a video amplifier 927, the synchronous detector 930, and the low pass filter 932, according to the manner described with reference to FIGS. 4 and/or 7. The signal processing board 960 may receive the output from the RF board 950 and may transform the signal to provide an output to the ADC converter 962.

It is contemplated that filtering, amplifying, and otherwise processing the signal received from the sensor may permit the detection and quantification of the target tissue temperature.

Example 1

One non-limiting example of the RF board 950 and its components is described below. In the example, the switch 904 may have a noise figure of about 3 dB and a gain of about −3 dB. The at least one circulator 922a,b may have a noise figure of about 1 dB. The LNA 924 may provide a noise figure of about 0.7 dB, a gain of about 20 dB, a power of 4 volts, and a current of about 45 mA. The RF HPF 916 and the RF LPF 928 may each provide a noise figure of about 1.5 dB and a gain of about −1.5 dB. The frequency mixer 944 may provide a noise figure of about 4 dB, a gain of about 2 dB, and a current of about 25 mA. The IF LPF 930 may provide a noise figure of about 2 dB and a gain of about −2 dB. Each of the IF amplifiers 922a,b may provide a noise figure of about 0.8 dB, a gain of about 18 dB, a power of about 4 volts, and a current of about 4 mA. Each of the at least one IF BPF 934a,b,c may have a noise figure of about 2 dB and gain of about −2 dB.

The device is contemplated to be relatively small in size. This may permit the device to be utilized in a plurality of applications, such as with children and infants, where there is a limited area for detection and for the sensor antenna to adhere to. Further, in many clinical settings, in particular the NICU, bulky equipment is hard to manage given the small size of the patient, and limiting the overall size of the device increases its ability to be utilized. As a result, each of the components in the device, such as all the components within the radiometer may be restricted in size and may, in some embodiments, be limited by the size restraints of the device. Thus, the placement and interaction of components in the system is contemplated to permit the processing of the signal as described. Of course, the placement and interactions may vary in some embodiments.

The device may be configured to convert the signal processed at the radiometer into a temperature reading. In some embodiments, the signal is converted into a numerical value corresponding to the temperature through an automated program. The program may be software, firmware, or other means for converting the signal.

The plurality of temperature readings during a cycle may be averaged and may return a temperature during the cycle. The temperature during the cycle may be displayed or otherwise communicated to a user as discussed herein.

For example, a cycle may be an hour in duration and one of the plurality of temperature readings may be taken every minute, the plurality of temperature readings collected during the cycle may be averaged and the average temperature may be recorded as the temperature during the hour. Of

TABLE 1

|   | Switch 904 | Circulator 922a, b | LNA 924 | RF HPF 926 | RF LPF 928 | Frequency Mixer 944 | IF LPF 930 | IF Amp. 922a | IF BPF 934a | IF Amp. 922b | IF BPF 934b | Total |
|---|---|---|---|---|---|---|---|---|---|---|---|---|
| Noise Figure (dB) | 3 | 4 | 4.7 | 4.72 | 4.74 | 4.85 | 4.87 | 4.89 | 4.89 | 4.89 | 4.89 | 4.89 |
| Gain (dB) | −3 | −4 | 16 | 14.5 | 13 | 15 | 13 | 31 | 29 | 47 | 45 | 63 |
| Pout (dBm) |  | −92.3 | −72.3 | −73.8 | −75.3 | −73.3 | −75.3 | −57.3 | −59.3 | −41.3 | −43.3 | −25.3 |
| Bias Current |  |  | 45 | 45 | 45 | 70 | 70 | 74 | 74 | 78 | 78 | 82 |

Table 1 illustrates the cumulative performance of each of the components of the RF board 950 as described. The table illustrates the cumulative noise figure, gain, output power ($P_{out}$), and bias current in the RF board 950 following each component. The cumulative total for each component in the RF board 950 results in a noise figure of 4.89 dB, a gain of 63 dB, a $P_{out}$ of −25.3 dBm, and a bias current of 82 mA. It is contemplated that the cumulative performance may reduce the noise and other interference in the system and improve the signal-to-noise ratio by amplifying the input. The values provided above, while demonstrating a preferred embodiment, are for illustrative purposes. In other embodiments, such values may stray from the exact values provided above, as long as such values remain within the spirit of the disclosure.

Continuing with the example, the total voltage gain in the signal processor board 960 may be approximately 1400. The video amplifier 927 may, in the provided example, provide a gain of approximately 160. In some embodiments, the video amplifier 927 may provide an additional gain of approximately 4.5. The synchronous detector may provide a gain of about 0.5 and the LPF 932 may provide a gain of about 7.8. Further, the LPF 932 may provide a voltage offset of about 2.048 volts and a reduction in gain of 0.5.

course, for a given application, the cycle may comprise any number of temperature readings and may be taken over any period of time. However, in another embodiment, the cycle may be about thirty seconds in length and each of the plurality of temperature readings may be taken at an interval. Of course, any length of cycle is contemplated and the aforementioned are provided as non-limiting examples only.

In each cycle, the plurality of temperature readings may be analyzed to determine whether any of the plurality of temperature readings is outside of a range of temperatures. In some embodiments, temperatures in the range may be determined according to a standard deviation of the plurality of temperature readings recorded during the cycle. Of course, in other embodiments, the range may be pre-set or otherwise determined. Further, in some embodiments, the range may be determined from a combination of a pre-set range of temperatures and the standard deviation of the plurality of temperature readings.

In one embodiment, a temperature reading outside of the range may not be included in determining the temperature during the cycle. In another embodiment, if a temperature reading is outside of the range, an additional temperature reading during the cycle may be taken. For example, when the cycle comprises the set number of temperature readings, the cycle may continue until the set number of temperature readings have been collected within the temperature range. For example, the device may be used in a clinical setting to detect the temperature of an individual, such as an infant in the NICU, to detect and monitor their temperature. The range may comprise temperatures that the individual is likely to experience, for example from about 94° F. to about 102° F. Temperatures outside of the range may be indicative of a false reading, for example, a reading of 70° F. may correspond to interference with the ambient temperature and, as the reading is outside of the range, would not be utilized to determine the temperature.

However, in another embodiment, the temperature may be determined from a singular temperature reading.

In some embodiments the device may comprise a digital display. The digital display may be configured such that it displays the temperature reading to a user. In one embodiment, the digital display may be any of an LCD display, LED display, segment display, or any other display that may be contemplated.

In a further embodiment, the device may be electronically coupled to an electronic device, such as an output monitor or computing device. Any manner of coupling the device to the electronic device is contemplated. For example, in one embodiment the coupling may utilize a YSI 400 standard thermistor adapter probe to couple the device to the electronic device. It is contemplated that coupling the device may, in some embodiments, require a non-linear resistance from a digital input to permit the coupling. In one embodiment, the coupling may utilize a digital potentiometer to provide variable resistance between the device and the electronic device.

It is contemplated that determining whether a temperature from the plurality of temperature readings is outside the range and removing that temperature from analysis may prevent environmental factors, such as noise, from negatively influencing the resulting temperature measurement.

Aspects of the present disclosure relate to an apparatus for measuring a target tissue temperature including: a sensor antenna including an outside and a contact side; a sensor antenna measurement aperture disposed on the contact side, the sensor antenna measurement aperture configured to generate a first signal; a skin temperature sensor disposed on the contact side, the skin temperature sensor configured to generate a second signal; and a radiometer, configured to receive the first signal and the second signal, in electrical communication with the sensor antenna, the sensor antenna measurement aperture, and the skin temperature sensor, wherein the radiometer includes at least one circulator, a radiofrequency (RF) board, and a signal processing board.

Aspects of the present disclosure relate to an apparatus, further including a remote switch module disposed between the sensor antenna and the radiometer.

Aspects of the present disclosure relate to an apparatus, wherein the RF board includes a low noise amplifier, an RF high pass filter, an RF low pass filter, an oscillator, a frequency mixer, an intermediate frequency (IF) low pass filter, an IF high pass filter, at least one IF band pass filter and at least one intermediate frequency amplifier, and an IF detector.

Aspects of the present disclosure relate to an apparatus, wherein the low noise amplifier includes a noise floor and amplifies the first and second signal.

Aspects of the present disclosure relate to an apparatus, wherein the target tissue temperature is proportional to the summation of $Td*A*e^{(-d/c1)}$ from the patient's skin to the target tissue, where d is the variable depth of a tissue, Td is the temperature at a depth d, A is a constant, c1 is a constant.

Aspects of the present disclosure relate to an apparatus, wherein the signal processing board includes a video amplifier, a synchronous detector, and a low pass filter.

Aspects of the present disclosure relate to an apparatus, wherein the radiometer selects a frequency of 4 gHz.

Aspects of the present disclosure relate to an apparatus, wherein the target tissue temperature is determined as an average tissue target tissue temperature detected during a cycle.

Aspects of the present disclosure relate to an apparatus, wherein the radiometer filters any of the first and second signals to reduce noise.

Aspects of the present disclosure relate to an apparatus, further including a digital display that displays the target tissue temperature.

Aspects of the present disclosure relate to a method to measure a target tissue temperature including: disposing a sensor antenna on a patient's skin, the sensor antenna including a sensor antenna measurement aperture and a skin temperature sensor; detecting, via the sensor antenna, a first signal including plurality of microwave emissions from a measurement volume of tissues, the measurement volume of tissues including a plurality of tissue layers; detecting, via the skin temperature sensor, a second signal corresponding to a patient's skin temperature; transmitting the first and second signal to a radiometer as a sensor input; processing, via the radiometer, the input, wherein the radiometer includes at least one circulator, a radiofrequency (RF) board, and a signal processing board; calculating, via the radiometer, an average temperature of the measurement volume of tissues from the sensor input; and calculating the target tissue temperature via the equation: Ttarget=Tskin+(Taverage−Tskin)*c, wherein Ttarget is the target tissue temperature, Tskin is the patient's skin temperature, Taverage is the average temperature, and c is a constant.

Aspects of the present disclosure relate to a method, wherein the sensor input is 4100±30 MHz and the RF board has an output of 100 Hz.

Aspects of the present disclosure relate to a method, wherein the average temperature is a weighted average temperature, calculated by weighing the average temperature based on an attenuation level of each of the plurality of tissue layers.

Aspects of the present disclosure relate to a method, wherein an adhesive is disposed on the sensor antenna.

Aspects of the present disclosure relate to a method, wherein the RF board includes a low noise amplifier, an RF high pass filter, an RF low pass filter, an oscillator, a frequency mixer, an intermediate frequency (IF) low pass filter, an IF high pass filter, at least one IF band pass filter and at least one intermediate frequency amplifier, and an IF detector.

Aspects of the present disclosure relate to a method, wherein the low noise amplifier sets a noise floor and amplifies the sensor input to be processed.

Aspects of the present disclosure relate to a method, wherein the signal processing board includes a video amplifier, a synchronous detector, and a low pass filter.

As described above, improved noninvasive temperature measuring technology is crucial, especially in neonatal ICU settings due to its non-disruptive nature, allowing for continuous monitoring without the risks of invasive methods. In neonates, conventional noninvasive temperature measuring devices often compound errors, primarily because of the high variability in surface body temperatures, the neonates' sensitivity to environmental temperature fluctuations, and the cumbersome attachment methods of conventional temperature measuring devices. Thus, these inaccuracies (which may be present in adult applications but exasperated in neonate applications, for the reasons listed above) can lead to significant accuracy departure from traditional invasive temperature measurements. To both mitigate these errors and provide a system physically suitable for neonates, it is essential to practice both the algorithmic steps described above and the hardware setup depicted above and in the figures herewith.

Although the apparatus is particularly useful for neonates due to its compact and noninvasive nature, it can also be effectively used in children and adults. The design described herein elicits improvements for accurate temperature measurement across various age groups, enhancing its utility in diverse clinical settings.

Attaching a cumbersome temperature measurement device to a neonate is challenging due to their small size, fragility, need to be frequently handled and cared for, and poor cooperation. Such conventional and bulky devices can cause discomfort and complicate caregiving tasks (e.g., bathing, feeding, etc.). Distributing the components of an improved temperature measurement device into separate portions (e.g., a sensor antenna and/or remote switch module separate from the radiometer housing) can alleviate these problems by decreasing the weight that would otherwise rest on the patient. The system design described above provides improved attachment, which allows for better and more consistent readings. Specifically, decreasing the weight and size of the portion of the system that resides on the neonate allows the interface between the neonate's skin and the sensor antenna to be continuous and, therefore, improve temperature readings. In one embodiment, the sensor antenna is separable from the remote switch module. In such an embodiment, the remote switch module may reversibly interface with the sensor antenna. Accordingly, the sensor antenna may be adhered to the skin of a patient and the remote switch module may be removed from the sensor antenna, permitting the sensor antenna to remain adhered to the patient's skin. This way, manipulation and repositioning of the patient is more feasible, as this tether to the sensor antenna may be reversibly removed and attached. Yet further, allowing the sensor antenna to remain affixed to the patient's skin in the same position (as opposed to removing the remote switch module and the sensor antenna and reapplying both components in a different position) permits the reading to be consistent because the sensor antenna remains indexed at the same point, even if the remote switch module is removed and reattached several times.

While this invention has been described in conjunction with the embodiments outlined above, many alternatives, modifications and variations will be apparent to those skilled in the art upon reading the foregoing disclosure. Accordingly, the embodiments of the invention, as set forth above, are intended to be illustrative, not limiting. Various changes may be made without departing from the spirit and scope of the invention.

What is claimed is:

1. An apparatus for measuring a target tissue temperature comprising:
    a sensor antenna including an outside and a contact side;
    a sensor antenna measurement aperture disposed on the contact side, the sensor antenna measurement aperture configured to generate a first signal;
    a skin temperature sensor disposed on the contact side, the skin temperature sensor configured to generate a second signal; and
    a radiometer, configured to receive the first signal and the second signal, in electrical communication with the sensor antenna, the sensor antenna measurement aperture, and the skin temperature sensor, wherein the radiometer comprises at least one circulator, a radiofrequency (RF) board, and a signal processing board, wherein the RF board comprises a low noise amplifier, an RF high pass filter, an RF low pass filter, an oscillator, a frequency mixer, an intermediate frequency (IF) low pass filter, an IF high pass filter, at least one IF band pass filter and at least one intermediate frequency amplifier, and an IF detector.

2. The apparatus of claim 1, further comprising a remote switch module disposed between the sensor antenna and the radiometer.

3. The apparatus of claim 1, wherein the low noise amplifier comprises a noise floor and amplifies the first and second signal.

4. The apparatus of claim 1, wherein the signal processing board comprises a video amplifier, a synchronous detector, and a low pass filter.

5. The apparatus of claim 1, wherein the target tissue temperature is determined as an average tissue target tissue temperature detected during a cycle.

6. The apparatus of claim 1, wherein the radiometer filters any of the first and second signals to reduce noise.

7. The apparatus of claim 1, further comprising a digital display that displays the target tissue temperature.

* * * * *